US010639022B2

(12) United States Patent
Keach et al.

(10) Patent No.: US 10,639,022 B2
(45) Date of Patent: May 5, 2020

(54) ENDOSCOPIC ORGAN MANIPULATION DEVICES AND METHODS

(71) Applicant: W. L. Gore & Associates, Inc., Newark, DE (US)

(72) Inventors: David C. Keach, Newark, DE (US); Nathan K. Mooney, Elkton, MD (US)

(73) Assignee: W. L. Gore & Associates, Inc., Newark, DE (US)

( * ) Notice: Subject to any disclaimer, the term of this patent is extended or adjusted under 35 U.S.C. 154(b) by 0 days.

(21) Appl. No.: 15/338,759

(22) Filed: Oct. 31, 2016

(65) Prior Publication Data

US 2017/0119365 A1 May 4, 2017

Related U.S. Application Data

(60) Provisional application No. 62/250,081, filed on Nov. 3, 2015.

(51) Int. Cl.
*A61B 17/02* (2006.01)
*A61F 2/04* (2013.01)
*A61B 17/00* (2006.01)
*A61M 25/09* (2006.01)

(52) U.S. Cl.
CPC .... *A61B 17/0218* (2013.01); *A61B 17/00234* (2013.01); *A61F 2/04* (2013.01); *A61B 2017/00296* (2013.01); *A61B 2017/00358* (2013.01); *A61B 2017/00526* (2013.01); *A61B 2017/00867* (2013.01); *A61B 2017/0225* (2013.01); *A61M 2025/09125* (2013.01)

(58) Field of Classification Search
CPC ..... A61B 17/11; A61B 17/234; A61B 17/218; A61B 2017/00867; A61M 25/09–0905
See application file for complete search history.

(56) References Cited

U.S. PATENT DOCUMENTS

| | | | | |
|---|---|---|---|---|
| 5,728,122 A | * | 3/1998 | Leschinsky | A61B 17/0057 604/526 |
| 7,048,695 B1 | * | 5/2006 | Schwager | A61M 25/09 600/585 |
| 7,678,123 B2 | | 3/2010 | Chanduszko | |
| 8,328,877 B2 | * | 12/2012 | Gellman | A61M 27/008 604/8 |
| 8,357,193 B2 | | 1/2013 | Phan | |
| 9,173,644 B2 | * | 11/2015 | Voss | A61B 17/0057 |

(Continued)

FOREIGN PATENT DOCUMENTS

| | | |
|---|---|---|
| WO | WO-2004112615 A2 | 12/2004 |
| WO | WO-2010138277 A1 | 12/2010 |
| WO | WO-2012058244 A2 | 5/2012 |

OTHER PUBLICATIONS

International Search Report and Written Opinion from PCT/US2016/059846, dated Feb. 9, 2017, 14 pages.

*Primary Examiner* — Nicholas J Plionis
*Assistant Examiner* — Steven J Cotroneo

(57) ABSTRACT

Retraction guidewires are disclosed, including retraction guidewires configured to transition from an elongate configuration for delivery to a treatment site through an organ wall to a deployed configuration for retraction of the organ wall, for example. The deployed configuration includes a stem portion and a dome portion having a distal end and a proximal end, the stem portion extending proximally from the distal end of the dome portion.

12 Claims, 6 Drawing Sheets

(56) References Cited

U.S. PATENT DOCUMENTS

| | | | | |
|---|---|---|---|---|
| 9,314,208 B1* | 4/2016 | Altmann | | A61B 5/6858 |
| 2004/0254602 A1* | 12/2004 | Lehe | | A61F 2/013 |
| | | | | 606/200 |
| 2005/0033361 A1* | 2/2005 | Galdonik | | A61B 17/0057 |
| | | | | 606/213 |
| 2006/0064114 A1* | 3/2006 | Obitsu | | A61B 17/221 |
| | | | | 606/113 |
| 2008/0194993 A1* | 8/2008 | McLaren | | A61M 25/09 |
| | | | | 600/585 |
| 2009/0018526 A1* | 1/2009 | Power | | A61M 25/09 |
| | | | | 604/508 |
| 2009/0143713 A1* | 6/2009 | Van Dam | | A61B 17/11 |
| | | | | 604/9 |
| 2010/0268029 A1 | 10/2010 | Hoang | | |
| 2011/0130756 A1* | 6/2011 | Everson, Jr. | | A61B 17/221 |
| | | | | 606/41 |
| 2011/0202077 A1 | 8/2011 | Chin | | |
| 2012/0109277 A1 | 5/2012 | Lupulu | | |
| 2012/0130417 A1 | 5/2012 | Lupulu | | |
| 2014/0257069 A1* | 9/2014 | Eliason | | A61B 5/6858 |
| | | | | 600/373 |
| 2014/0350524 A1* | 11/2014 | O'Day | | A61M 25/09 |
| | | | | 604/509 |
| 2015/0313599 A1* | 11/2015 | Johnson | | A61B 17/12022 |
| | | | | 606/191 |
| 2016/0113582 A1* | 4/2016 | Altmann | | A61B 5/6858 |
| | | | | 600/374 |
| 2016/0135813 A1* | 5/2016 | Johnson | | A61B 17/0057 |
| | | | | 606/213 |
| 2016/0278796 A1* | 9/2016 | Gehle | | A61B 17/221 |

* cited by examiner

ENDOSCOPIC ORGAN MANIPULATION DEVICES AND METHODS

BACKGROUND

Drainage is a common therapeutic approach to manage many malignant and benign GI diseases that result from a blocked or strictured lumen. Some examples include but are not limited to biliary drainage due to malignant or benign biliary obstruction of the common bile duct, duodenal drainage due to benign or malignant duodenal stenosis, and transpapilary gallbladder drainage due to gallstone induced acute cholecystitis.

Drainage can be performed using surgical, percutaneous laparoscopic and endoscopic techniques. Historically endoscopic drainage techniques have generally been limited to native lumen internal drainage only, e.g., transpapilary or within the GI tract itself. If the native lumen could not be endoscopically accessed to provide drainage, the patient was typically referred to the interventional radiologist for percutaneous drainage, or as a last resort to the surgeon. Recent advances in endoscopic ultrasound (EUS) have offered less invasive transmural internal drainage alternatives (e.g., going outside the native lumen) for percutaneous or surgical drainage techniques.

Current delivery systems for stents in transmural EUS internal drainage applications face several challenges, including the risk of leak outside of the native lumen that can result in severe morbidity or mortality as well as complexity of the delivery system that make the procedure cumbersome and time consuming. Drainage devices can be used for internal drainage between various organs. Some of the envisioned options are duodenum-CBD, gastric-hepatic, gastric-jejunum, gallbladder-duodenum, gallbladder-jejunum, and gastric-pancreas. Various complications may arise in the delivery and use of drainage systems. For example, perforating the walls of organs during delivery of drainage systems can result in the contents contained within that organ to migrate into areas of the body which are not tolerant of the leaked contents. To mitigate the risk of leaks, the walls of the two organs being perforated can be forced in to direct contact with each other, so that organ contents will pass from one organ in to the other, and not into unintended anatomy. Various procedures include use of a thin needle to penetrate, and thus fenestrate, the organs (e.g., under continuous real-time ultrasound guidance).

SUMMARY

Various inventive aspects of the instant disclosure facilitate delivery mechanisms that mitigate the risk of complications and facilitate safe and effective delivery of devices for transmural procedures. Some aspects of the instant disclosure relate to retraction guidewires configured to transition from an elongate configuration to a deployed configuration. The deployed configuration includes a stem portion and a dome portion having a distal end and a proximal end, the stem portion extending proximally from the distal end of the dome portion.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

While various embodiments are shown in the figures, additional and alternative features to those shown are provided by the instant disclosure.

DETAILED DESCRIPTION

Various embodiments relate to retraction guidewires for delivery systems, such as endoscopic delivery systems. Use of retraction guidewires that are made of a fine, or small diameter, wires facilitate use of fine needles (e.g., a hollow endoscopic ultrasound fine needle) to deploy the retraction guidewire. In turn, clinicians or other users are able to deploy the retraction guidewire through smaller fenestrations. In some embodiments, the retraction guidewires are deployed from an elongate configuration to a domed configuration, also described as inverted cup or concave configuration, with crossing wire segments that allow the user to impart a substantial retraction force on the organ wall with a thin wire. Although such features find a variety of uses, in some embodiments the retraction guidewire is utilized to draw a first wall of a first organ into contact with a second wall of a second organ in association with a surgical procedure, such as transmural endoscopic ultrasound (EUS) internal drainage applications. Various embodiments are described in association with nickel-titanium alloy wires ("NiTi wires"), although a variety of materials (e.g., stainless steel or shape memory polymers) are contemplated.

Figure 1:
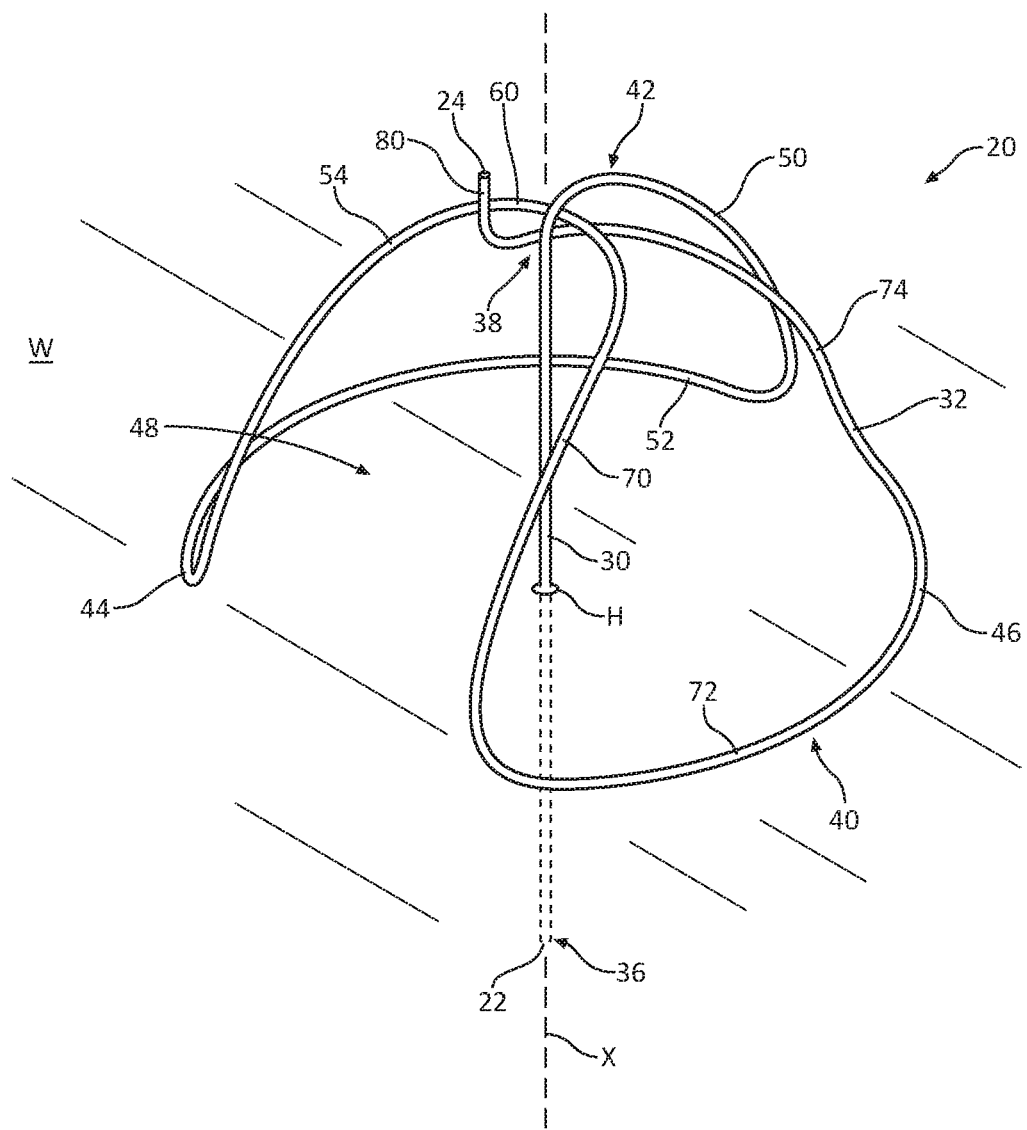
FIG. 1 is an isometric view of a retraction guidewire in a deployed state, according to some embodiments.

FIG. 1 is an isometric view of a retraction guidewire 20 in a deployed state, according to some embodiments. As shown, the retraction guidewire 20 is formed of a single wire, or filament, extending from a first end 22 to a second end 24 and treated (e.g., heat treated using one or more mandrels) to transition elastically from a relatively elongate configuration (e.g., when maintained inside a fine needle) and a deployed configuration for engaging an organ wall W. Although single filaments are shown and described, and can be particularly advantageous as mentioned above, it should also be understood that braided or other multi-filament guidewire configurations are also contemplated. For example, as an alternative to a monolithic filament, or monofilament, the guidewire 20 can be formed of a tightly braided, plurality of filaments. The guidewire 20 is optionally formed of a superelastic alloy, such as a nickel-titanium alloy, although other materials are also contemplated as previously referenced. The guidewire 20 also optionally includes coatings (e.g., ePTFE membrane overwraps or other features) or surface treatments, for example, as desired.

In the deployed configuration, the guidewire 20 extends through a relatively tortuous path to define a stem 30, or stem portion 30, (shown extending through an aperture in the organ wall W) and a dome 32, or dome portion 32, a bottom surface of which is shown engaged the organ wall W.

As shown, the stem 30 is biased to extend in a relatively elongate configuration in a longitudinal direction, which is a proximal-distal direction as the terms "proximal" and "distal" are used herein. The stem 30 defines a proximal end 36, a distal end 38, and a central longitudinal axis X of the overall shape of the guidewire 20 in the deployed configuration, although offsets (both angular and/or lateral offsets) are contemplated.

Figure 2:
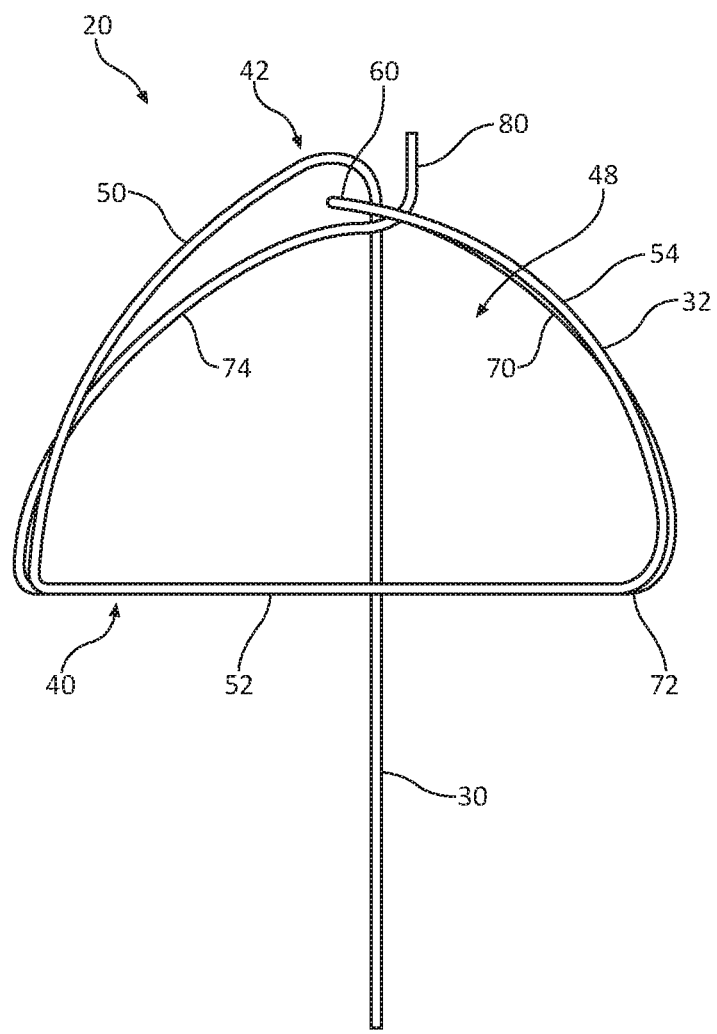
FIG. 2 is side view of the retraction guidewire of FIG. 1, according to some embodiments.
Figure 3:
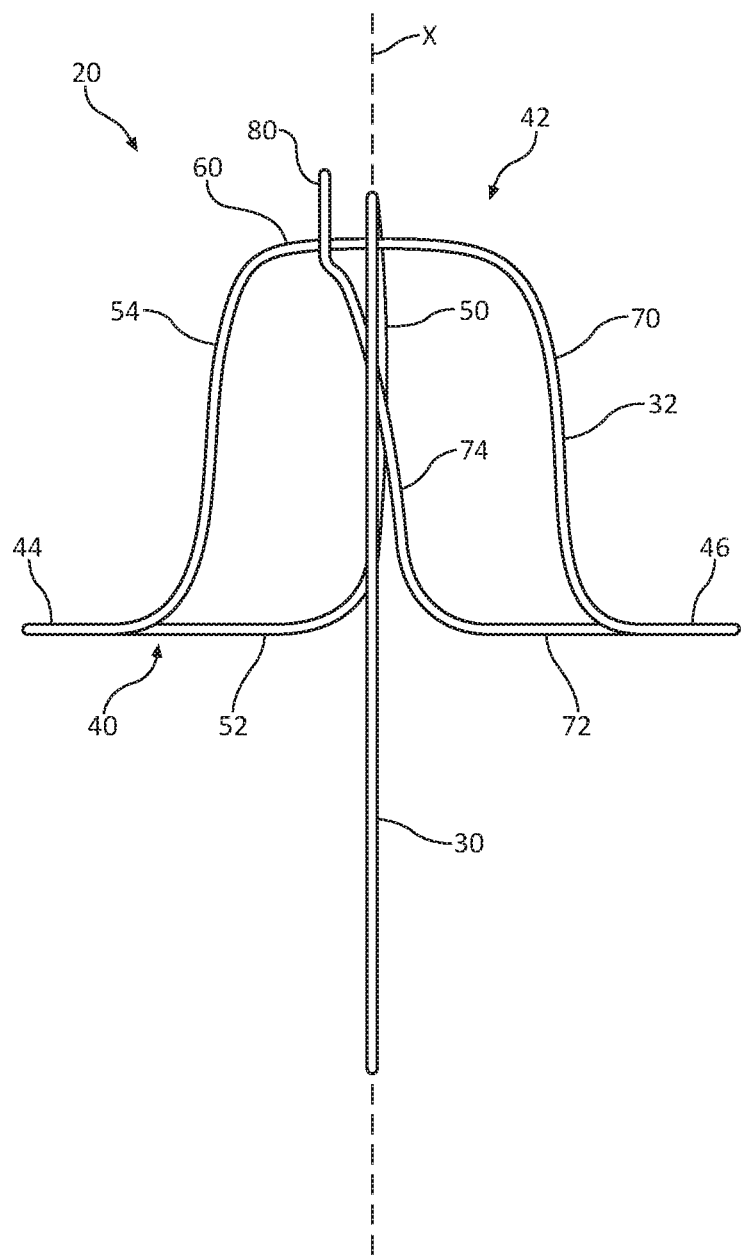
FIG. 3 is a front view of the retraction guidewire of FIG. 1, according to some embodiments.
Figure 4:
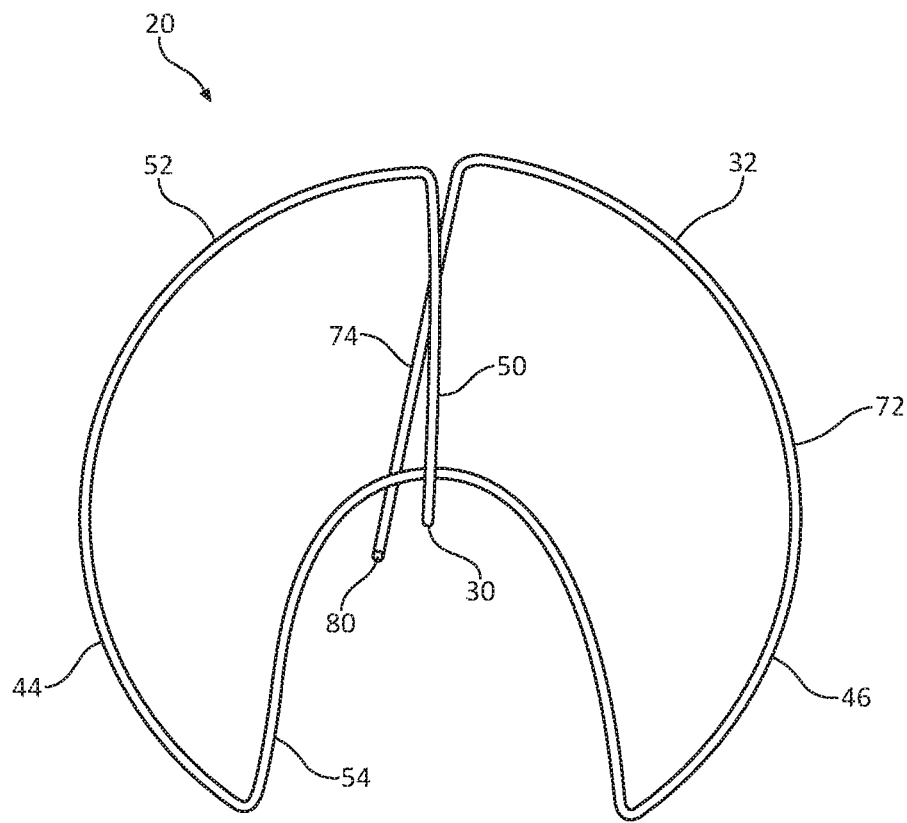
FIG. 4 is a top view of the retraction guidewire of FIG. 1, according to some embodiments.

FIGS. 2, 3, and 4 illustrate the retraction guidewire 20 in the deployed state (also described as an expanded state) from side, front, and top views, respectively, according to some embodiments. As shown, the dome 32 approximates, or otherwise defines a generally semi-circular profile (a half-circle) when viewed from the side (FIG. 2), a bell shape when viewed from the front (FIG. 3), and a three-quarter circular profile (with an arcuate relief) when viewed from the top (FIG. 4). In describing various segments, or portions, of the retraction guidewire 20, the side view of FIG. 2 is considered to be facing the X-Z plane (or simply "X-plane"), the front view of FIG. 3 is considered to be facing the Y-Z plane (or simply "Y-plane"), and the top view of FIG. 4 is considered to be facing the X-Y plane (or simply the "Z-plane").

In some embodiments, the dome 32 of the retraction guidewire 20 generally defines a proximal end 40, a distal end 42, a first lobe 44, also described as a first contact loop, and a second lobe 46, also described as a second contact loop. The dome portion also defines an open interior 48 through which the stem portion 30 extends. The dome 32 includes a plurality of crossing wire segments such that upon retraction of the stem portion 30, a collapsing force is imparted on the first and second lobes 44, 46, which resiliently resist collapsing. In this manner, the retraction guidewire 20 translates a resilient retraction force to the proximal end 40 of the dome portion 32 for retraction of the organ wall W.

In some embodiments, the first lobe 44 includes a first leg portion 50, a first foot portion 52, and a second leg portion 54.

As shown in FIG. 2, in the X-plane the first leg portion 50 sweeps proximally from the distal end 38 of the stem 30 through an arcuate path. As shown in FIGS. 3 and 4, the first leg portion 50 extends generally linearly (is not substantially curved) in the Y- and Z-planes, although the first leg portion 50 does include radiused, or arcuate transitions to adjacent wire segments. The first leg portion 50 extends from the distal end 38 of the stem 30, over the second leg portion 54, and also over part of the second lobe 46.

In some embodiments, the first foot portion 52 extends arcuately from the first leg portion 50 to define a bottom contact surface at the proximal end 40 of the dome 32. As shown in FIGS. 2 and 3, in the X- and Y-planes the first foot portion 52 extends generally linearly, defining a relatively flat, bottom contact surface of the dome 32. As shown in FIG. 4, the first foot portion 52 extends through an arcuate path in the Z-plane (e.g., less than 180 degrees). The radius of the first foot portion 52 relative to the stem 30 is about 20 mm (corresponding to an overall diameter of the dome portion of about 40 mm), for example, although a variety of dimensions are contemplated. The first foot portion 52 also includes radiused, or arcuate transitions to adjacent wire segments.

In some embodiments, the second leg portion 54 extends distally up from the first foot portion 52. As shown in FIG. 2, the second leg portion 54 extends in an arcuate path in the X-plane. As shown in FIG. 3, the second leg portion 54 is recurved, or defines an S-shape in the Y-plane, extending from the first foot portion 52 into the second lobe 46. As shown in FIG. 4, in the Z-plane the second leg portion 54 extends generally linearly upwardly from the first foot portion 52, although arcuate paths are contemplated, and then transitions into the second lobe 46 through an arcuate transition 60 that passes under the first leg portion 50 where the first leg portion 50 transitions from the stem 30. In some embodiments, the arcuate transition has a radius of about 8 mm, although a variety of dimensions are contemplated. The second leg portion 54 also includes radiused, or arcuate transitions to adjacent wire segments.

In some embodiments, the second lobe 46 includes a third leg portion 70, a second foot portion 72, and a fourth leg portion 74.

As shown in FIG. 1, the third leg portion 70 extends proximally down from the second leg portion 54 of the first lobe 44. As shown in FIG. 2, the third leg portion 70 (partially hidden) extends in an arcuate path in the X-plane. As shown in FIG. 3, the third leg portion 70 is recurved, or defines an S-shape in the Y-plane, extending from the second leg portion 54 of the first lobe 44. The third leg portion 70 transitions from the second leg portion 54 through the arcuate transition 60 that passes under the first leg portion 50. As shown in FIG. 4, in the Z-plane, the third leg portion 70 extends generally linearly downwardly to the second foot portion 72 from the second leg portion 54, although arcuate pathways are contemplated. The third leg portion 70 also includes radiused, or arcuate transitions to adjacent wire segments.

In some embodiments, the second foot portion 72 extends arcuately from the third leg portion 70 to define a bottom contact surface at the proximal end 40 of the dome 32. As shown in FIGS. 2 and 3, in the X- and Y-planes the foot portion 72 (largely hidden in FIG. 2) extends generally linearly, defining a relatively flat, bottom contact surface of the dome portion 32. As shown in FIG. 4, the second foot portion 72 extends through an arcuate path in the Z-plane (e.g., less than 180 degrees). The radius of the second foot portion 72 relative to the stem 30 is about 20 mm, for example, although a variety of dimensions are contemplated. Thus the width of the dome 32 from the Z-plane (FIG. 4), or the footprint of the guidewire 20, is about 40 mm at the proximal end 40, according to some embodiments, although a variety of dimensions are contemplated. In different terms, the guidewire 20 exhibits a crossing profile ratio from the collapsed to the expanded configuration of greater than 1:40, according to some embodiments (e.g., a less than 1 mm diameter guidewire transitioning to a complex shape having a diameter of about 40 mm). The second foot portion 72 also includes radiused, or arcuate transitions to adjacent wire segments. In some embodiments, the various radiused transitions of the foot portions 52, 74, for example, help ensure that the dome portion 32 is atraumatic in the deployed configuration, and does not otherwise penetrate or puncture tissue.

As shown in FIG. 2, in the X-plane the fourth leg portion 74 sweeps distally up from the second foot portion 72 through an arcuate path. As shown in FIGS. 3 and 4, the fourth leg portion 74 extends generally linearly (is not substantially curved) in the Y- and Z-planes, although the fourth leg portion 74 does include radiused, or arcuate transitions to adjacent wire segments. As shown in the figures, the fourth leg portion 74 passes under the first leg portion 50 at an intermediate position between the proximal end 40 and the distal end 42 of the dome 32. For example, the fourth leg portion 74 travels a somewhat angled path in the Y-plane (FIG. 3) relative to the central longitudinal axis X of the guidewire 20. The fourth leg portion 74 also extends under the second leg portion 54 at the distal end 42 of the dome 32. As shown, the fourth leg portion 74 extends under the second leg portion 54 near (e.g., within about 5 mm) of where the second leg portion 54 passes under the first leg portion 50.

As shown, the fourth leg portion 74 terminates in an upwardly swept, distally extending segment 80, also described as a hook 80. The upwardly swept hook 80, which corresponds to the distal end 24 of the guidewire 20, can act as a locking, or securing mechanism to help align the wire segments and define the positions of the crossing points (also described as a plurality of crossing segments of the guidewire), and the overall shape of the guidewire 20 in the deployed, or expanded state.

Various methods are contemplated for deploying the guidewire 20 from a relatively elongate configuration (e.g., when maintained inside a fine needle) and the deployed configuration for engaging an organ wall. In some embodiments, a fine needle (e.g., a EUS fine needle) (not shown) is utilized under endoscopic guidance to puncture the wall W of an organ (e.g., a gall bladder) to form a fenestration H (FIG. 1). The guidewire 20 is delivered to the fenestration with the fine needle, in which it is contained in a substantially collapsed (e.g., generally elongate) configuration. For reference, the term "elongate configuration" includes more simple geometries (e.g., a line or an arc) rather than more complex shapes, such as that of the dome portion 32 shown in the figures.

The guidewire 20 is deployed from the needle and sequentially deploys beginning with the distal end 24 of the guidewire 20. For example, the guidewire 20 elastically recovers its shape beginning with the hook 80 and then snaking into its final, complex shape beginning at the distal end 24 of the guidewire and ending with the stem 30. The stem 30 is of a sufficient length to allow a user to impart a tension on it and thus provides a means for applying tension to the dome 32 from outside the organ, through the wall, through a very small fenestration H. That tension is able to be used to retract the wall W of the organ, according to some embodiments. In some examples, the guidewire has a maximum diameter of 0.8 mm, facilitating a relatively small fenestration, although a variety of dimensions, including smaller diameters, are contemplated.

Figure 5:
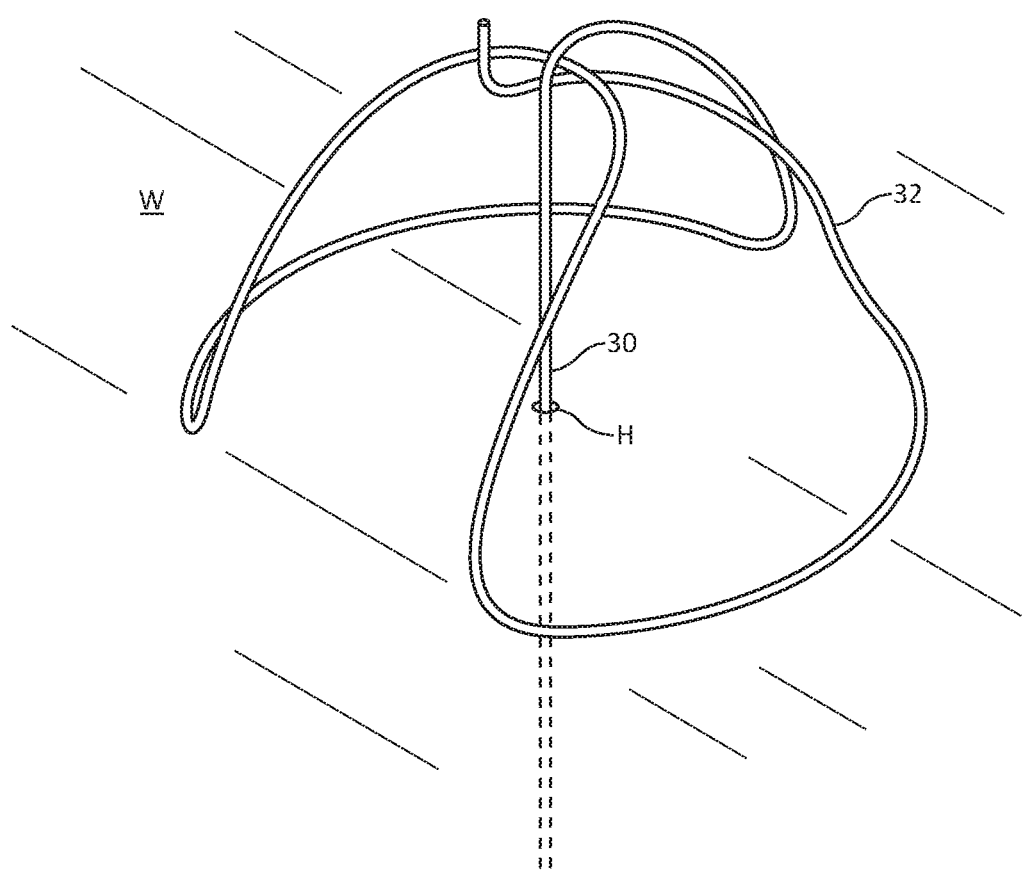
FIG. 5 is an isometric view of the retraction guidewire of FIG. 1 deployed through the fenestration in the organ wall and prior to retraction, according to some embodiments.
Figure 6:
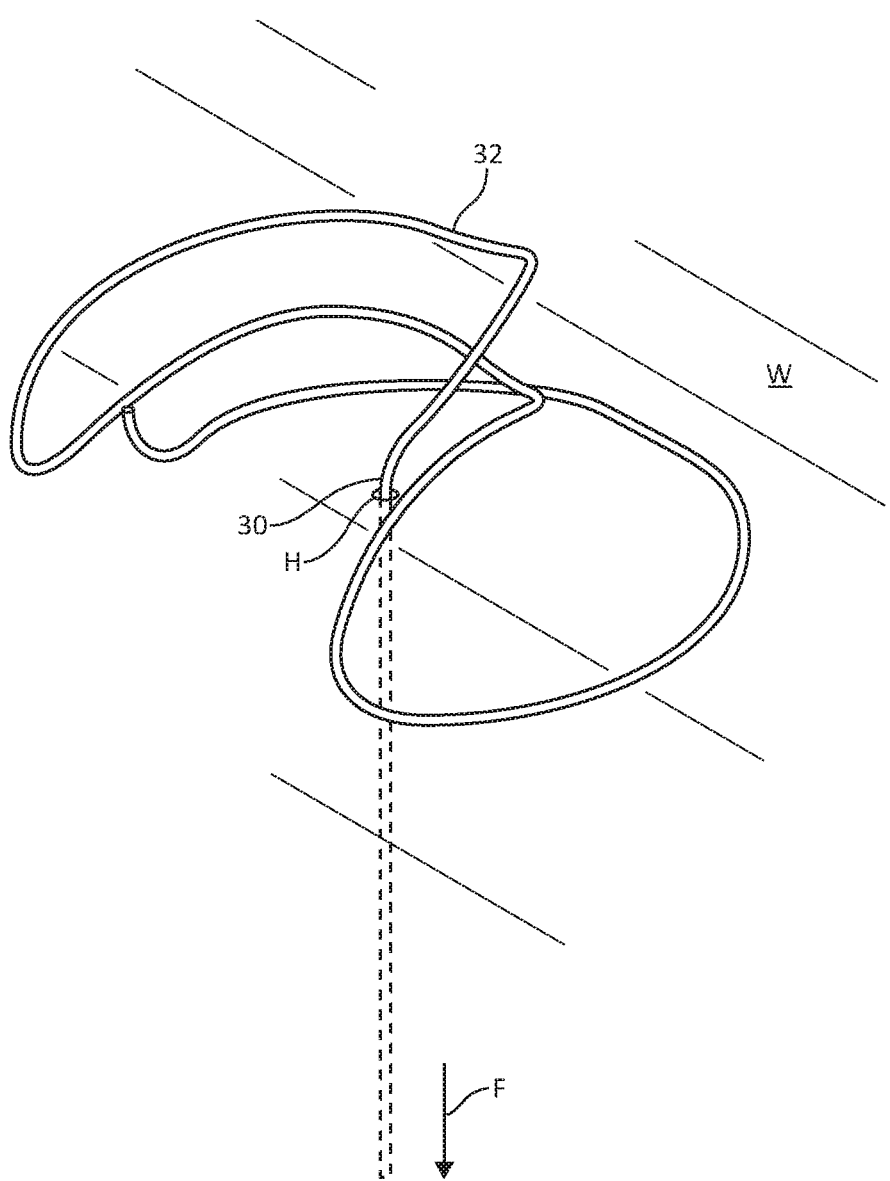
FIG. 6 is an isometric view of the retraction guidewire of FIG. 4 deployed through the fenestration in the organ wall and following retraction, according to some embodiments.

FIGS. 5 and 6 are illustrative of how the guidewire, following deployment, deforms with the application of a retraction force F (FIG. 6) applied to the stem 30. As shown by a comparison of FIG. 5 (without retraction force F) and FIG. 6 (with retraction force F), the various, crossing wire segments of the dome 32 resiliently resist collapse of the dome 32. Additionally, the relatively wide profile of the dome 32 in the Z-plane and in particular at the bottom contact surface at the proximal end 40, helps avoid stressing the fenestration during retraction (e.g., reducing the chance for tearing or leakage). The open interior 48 of the dome 32 and the aforementioned enlarged footprint also assist with delivery of a device (e.g., a drainage device) over the stem portion 30 of the guidewire 20 and into, or through the fenestration H as desired.

In some embodiments, in order to remove the guidewire 20, the needle or other delivery device (not shown) is reintroduced through the fenestration and the guidewire 20 is retracted into the delivery device and back to the collapsed configuration.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the above described features.

What is claimed is:

1. A retraction guidewire formed as a single, continuous length of material in which the guidewire defines a first end, a second end, and a length between the first end and the second end and is configured to transition from an elongate configuration to a deployed configuration, the single, continuous length of material between the first and second ends being configured to elastically recover from the elongate configuration to the deployed configuration in which the single, continuous length of material defines:
   a stem portion; and
   a dome portion having a distal end and a proximal end, the stem portion extending proximally within the dome portion from the distal end of the dome portion past the proximal end of the dome portion, the dome portion having a first side and a second side defined laterally opposite the first side, and the dome portion including,
      a first contact loop on the first side of the dome portion that extends from the distal end to the proximal end of the dome portion, and
      a second contact loop on the second side of the dome portion that extends from the distal end to the proximal end of the dome portion,
      the first contact loop including a first leg portion, a first foot portion, and a second leg portion, the first leg portion sweeping proximally from the stem through an arcuate path, the first foot portion extending arcuately from the first leg portion to define a bottom contact surface at a proximal end of the dome portion, and the second leg portion extending distally from the first foot portion.

2. The retraction guidewire of claim 1, wherein the proximal end of the dome portion defines a planar engagement surface for engaging a surface of an organ.

3. The retraction guidewire of claim 1, wherein the dome portion includes a second foot portion defined by an arcuate extension of wire at the proximal end of the dome portion.

4. The retraction guidewire of claim 1, wherein the dome portion defines an open interior region through which the stem portion extends.

5. The retraction guidewire of claim 1, wherein the dome portion and the stem portion are interconnected in a locking arrangement, the locking arrangement including a plurality of crossing segments of the retraction guidewire.

6. The retraction guidewire of claim 1, wherein the dome portion extends from the stem portion such that retraction of the stem portion in the proximal direction results in a compressive force on a plurality of crossing segments of the retraction guidewire at the distal end of the dome portion.

7. The retraction guidewire of claim 1, wherein the retraction guidewire has a distal end and a proximal end, and further wherein the distal end of the retraction guidewire is located at the distal end of the dome portion.

8. The retraction guidewire of claim 1, wherein the retraction guidewire is formed as a monolithic length of nickel-titanium filament.

9. The retraction guidewire of claim 1, wherein the retraction guidewire has an outer diameter of 0.8 mm or less.

10. The retraction guidewire of claim 1, wherein the first foot portion is spaced from the stem portion by a radial distance.

11. The retraction guidewire of claim 1, wherein the dome portion is atraumatic.

12. The retraction guidewire of claim 1, wherein the single, continuous length of material is configured sequentially deploy by snaking through a tortuous path into the deployed configuration starting at the first end and ending at the second end as the retraction guidewire is deployed from a delivery system.

* * * * *